(12) United States Patent
Kang et al.

(10) Patent No.: US 10,975,405 B2
(45) Date of Patent: Apr. 13, 2021

(54) METHOD FOR DO NOVO BIOSYNTHESIS OF CHONDROITIN SULFATE

(71) Applicant: Jiangnan University, Wuxi (CN)

(72) Inventors: Zhen Kang, Wuxi (CN); Jian Chen, Wuxi (CN); Guocheng Du, Wuxi (CN); Zhengxiong Zhou, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 303 days.

(21) Appl. No.: 15/808,944

(22) Filed: Nov. 10, 2017

(65) Prior Publication Data

US 2018/0135089 A1    May 17, 2018

(30) Foreign Application Priority Data

Nov. 14, 2016 (CN) .......................... 201610997085.4
Dec. 14, 2016 (CN) .......................... 201611149169.9

(51) Int. Cl.
  *C12N 11/08*    (2020.01)
  *C12P 19/26*    (2006.01)
  *C12N 9/10*    (2006.01)

(52) U.S. Cl.
  CPC ................ *C12P 19/26* (2013.01); *C12N 9/13* (2013.01); *C12Y 208/02005* (2013.01); *C12Y 208/02017* (2013.01)

(58) Field of Classification Search
  None
  See application file for complete search history.

(56) References Cited

PUBLICATIONS

Suglura et al. (JBC, vol. 297, No. 52, Dec. 2012, p. 43390-43400).*
Yamada et al. (Biochem. J., 2004, vol. 384, pp. 567-575).*

* cited by examiner

*Primary Examiner* — Hope A Robinson
(74) *Attorney, Agent, or Firm* — IPro, PLLC

(57) ABSTRACT

The present invention relates to a method for chondroitin sulfate biosynthesis, belongs to the field of pharmaceuticals. CS was biosynthesized by sulfating the chondroitin with C4ST or C6ST in Tris-HCl buffer assisted with 3'-phosphoadenosine 5'-phophosulfate (PAPS). C4ST and C46ST came from bioengineered *Escherichia coli* or *Pichia pastoris*. Chondroitin came from bioengineered *Bacillus subtilis* 168.

13 Claims, 6 Drawing Sheets
Specification includes a Sequence Listing.

METHOD FOR DO NOVO BIOSYNTHESIS OF CHONDROITIN SULFATE

The present application claims priority to CN 201610997085.4 filed on Nov. 14, 2016 and CN 201611149169.9 filed on Dec. 14, 2016.

TECHNICAL FIELD

The present invention relates to a method for chondroitin sulfate biosynthesis. The disclosure herein relates to the field of pharmaceuticals field.

BACKGROUND

Chondroitin sulfate (CS) belongs to glycosaminoglycan (GAG), is an anion, linear, and acidic polysaccharides with repeating disaccharides unit of alternative 1-4-glucuronic acid (GlcUA) and 1-3-N-acetylgalactosamine (GalNAc) with some sulfated modification. CS was structural heterogeneity and each disaccharides was sulfated differently: CSA=GlcUA-GalNAc(4S); CSC=6S, GlcUA-GalNAc(6S)); CSE=GlcUA-GalNAc(4S6S); CSK=GlcUA(3S)-GalNAc(4S), CSL=GlcUA(3S)-GalNAc(6S), and CSM=GlcUA(3S)-GalNAc(4,6S). Because of the physiological anti-inflammatory function, CSA and CSC have recently substituted the conventional nonsteroidal drugs for osteoarthritis treatment while CSE promote neurite outgrowth toward primary neurons and play an important role in anticoagulant activity of thrombomodulin as heparin.

All the CS applied in pharmacological was extracted from shark cartilages, bovine, and so on. However, another glycosaminoglycan, keratin sulfate, was the contaminant of the CS, and was hard to separate it from CS because of the similar structure during the extraction procedures. It limited the application of CS in other pharmacological industry other than as osteoarthritis drugs. What's worst, there may be a risk of acquiring mad cow disease after ingested chondroitin sulfate from bovine tissue (FDA). Therefore, several reports appeared in the documents for the synthesis of CS in the last few years with CS oligosaccharides synthesis. Sulfated modification was challenging to introduce sulfate groups to the specific position of oligosaccharides chains by chemical synthesis. So bioenzymatic method for CS was supposed to be an optimum method, which was mild, effective and specify as for HP and other glycosaminoglycan.

The synthesis of GAG by bioenzymatic method was divided into two parts: precursor synthesis, sulfated modification. The precursor was synthetized by kinds of glycosyltransferases and epimerases. However, the active sulfotransferase was supposed to be glycosylated modification during the process of protein maturation. But there was no glycosylated modification in prokaryote and different glycosylated modification in eukaryote. So these sulfotransferases were only expressed in some animal cells, such as COS cell, for a long time. So it was difficult in expressing the sulfotransferases in microbial cells. During the last decade, some reports in the document pointed that the sulfotransferase for HP synthesis was expressed with the active protein in yeast while these active sulfotransferases also need glycosylated modification. Therefore, the yeast was chosen to be host for C6ST, C4ST, and CHST 15 expressing. It was supposed to be a method for CS synthesis by bioenzymes and also may be will correct the application of CS in other pharmaceutical fields.

SUMMARY

A technical problem to be solved by the present invention is to provide a method for biosynthesis of CS.

The purpose of this invention is to provide a method for bioactive Chondroitin sulfate (CS) synthesis. CS is generated by sulfating chondroitin using C4ST (Chondroitin 4-sulfotransferase) or C6ST (Chondroitin 6-sulfotransferase) assisted with PAPS (3'-phosphoadenosine-5'-phosphosulfate) regeneration system.

In one embodiment of the present disclosure, C4ST and C6ST are produced by microorganisms heterogeneously expressing the gene encoding C4ST or C6ST from animals.

In one embodiment of the present disclosure, the host used to express C4ST or C6ST can be *Escherichia coli* or *Pichia pastoris*, accordingly, the plasmids used for recombinant expression can be pET or pPIC.

In one embodiment of the present disclosure, the sequence of gene encoding C4ST (SEQ ID NO:15) is recorded as Gene ID: 58250 in NCBI (National Center for Biotechnology Information Search database).

In one embodiment of the present disclosure, the sequence of gene encoding C6ST (SEQ ID NO:16) is recorded as Gene ID: 53374 in NCBI.

In one embodiment of the present disclosure, the PAPS regeneration system contains 0.1-100 µg ASST IV (Aryl sulfotransferase IV), 0.1-50 mM PNPS (p-nitrobenzenesulphonic acid), 1-200 µM PAP (3'5'-adenosine diphosphate) and 1-200 mM Tris-HCl (pH5-9). The PAPS regeneration system was used to catalyze PNPS to PAPS.

In one embodiment of the present disclosure, ASST IV (Gene ID: 83783 and SEQ ID NO:17) was expressed in *E. coli*. based on the plasmids of pET.

In one embodiment of the present disclosure, 0.1-100 µg C4ST or C6ST is added to PAPS regeneration system for CS synthesis.

In one embodiment of the present disclosure, specific activity of ASST IV is 0.1-100 nmol/min·mg·protein, specific activity of C4ST is 0.1-100 pmol/min·mg·protein, specific activity of C6ST is 0.1-100 pmol/min·mg·protein.

In one embodiment of the present disclosure, CS is generated by sulfating chondroitin using C4ST or C6ST assisted with PAPS regeneration system under 10-50° C.

In one embodiment of the present disclosure, CS is generated by sulfating chondroitin using C4ST or C6ST assisted with PAPS regeneration system under 25-50° C.

In one embodiment of the present disclosure, CS is generated by sulfating chondroitin using C4ST or C6ST assisted with PAPS regeneration system within 1-50 h.

In one embodiment of the present disclosure, CS is generated by sulfating chondroitin using C4ST or C6ST assisted with PAPS regeneration system within 20-50 h.

In one embodiment of the present disclosure, chondroitin is produced by recombinant *Bacillus subtilis* 168. The recombinant *B. subtilis* 168 is constructed by expressing KfoC and KfoA in genome and co-expressing genes related to the synthetic pathway of chondroitin, such as genes related to the synthetic pathway of UDP-glucuronic acid (UDP-GlcUA) or UDP-N-Acetylglucosamine (UDP-GlcNAc). Genes related to the synthetic pathway of UDP-GlcUA include pgcA, gtaB, tuaD. Genes related to the synthetic pathway of UDP-GlcNAc include glmS, glmM, glmU.

In one embodiment of the present disclosure, the recombinant *B. subtilis* 168 is constructed by expressing KfoC and KfoA in genome and co-expressing genes tuaD and glmU, or co-expressing genes tuaD, glmU, gtaB, glmM and glmS.

In one embodiment of the present disclosure, plasmid pP43NMK is used to express genes related to the synthetic pathway of chondroitin.

In one embodiment of the present disclosure, the recombinant B. subtilis 168 is cultivated at 37° C. for 24-60 h to produce chondroitin. Chondroitin can be collected form the supernatant of cultivation. The fermentation medium comprises 20 g/L yeast extract, 15 g/L or 50 g/L sucrose, 3.9 g/L $K_2SO_4$, 1.5 g/L $MgSO_4$ and 50 mM phosphate buffer, pH 6.5-7.5.

The present disclosure provides a method for expressing C4ST and C6ST in microorganisms and using C4ST and C6ST to synthesize Chondroitin sulfate (CS) for the first time. 10-30% of chondroitin was converted to CS which shows a great potential in industry application.

DETAILED DESCRIPTION

Figure 1:
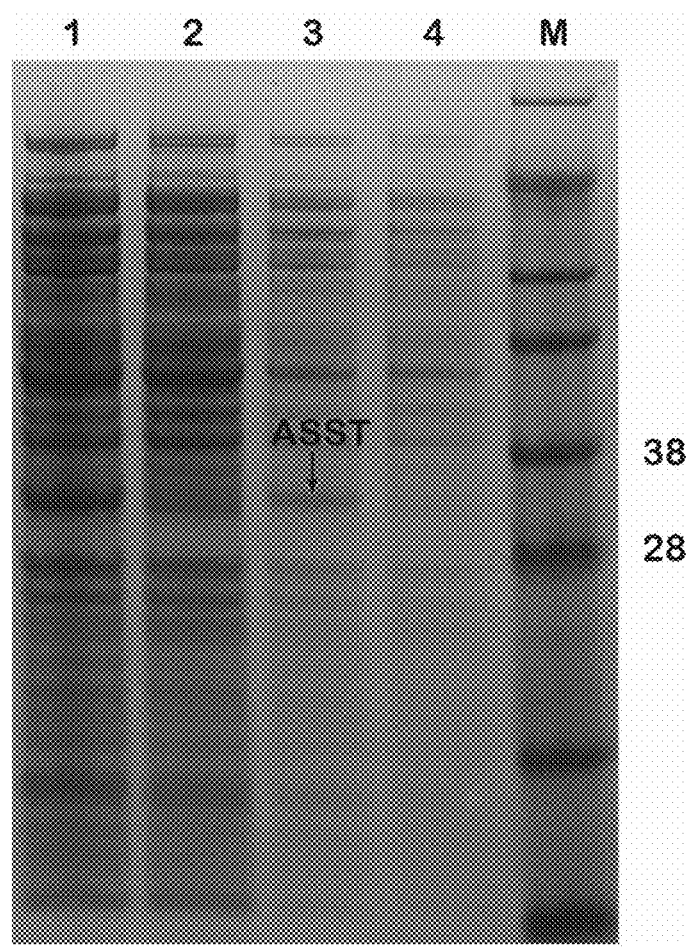
FIG. 1 SDS-PAGE analysis of recombinant E. coli which expressed ASST IV. M, marker; 1, SDS-PAGE analysis of whole cellular of E. coli BL21-pET20b-ASST IV; 2, SDS-PAGE analysis of whole cellular of E. coli BL21-pUC19-ASST IV; 3, SDS-PAGE analysis of the culture supernatant of E. coli BL21-pET20b-ASST IV; 4, SDS-PAGE analysis of the culture supernatant of E. coli BL21-pUC19-ASST IV.
Figure 2:
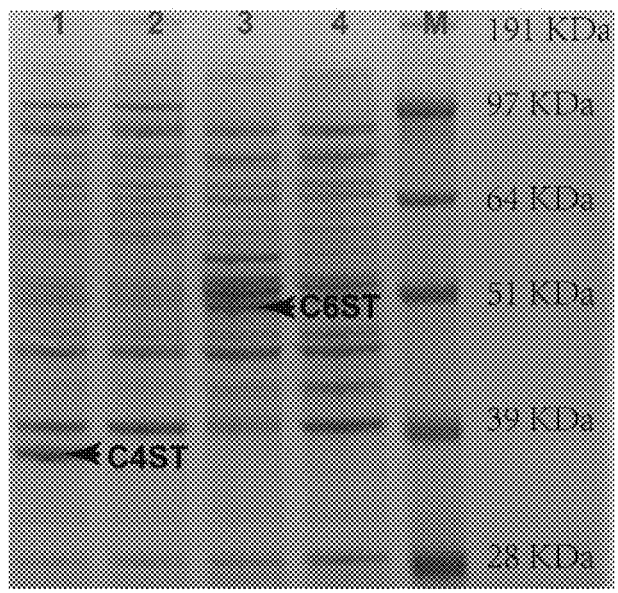
FIG. 2 SDS-PAGE analysis of recombinant E. coli which expressed C4ST or C6ST. M, marker; 1, SDS-PAGE analysis of culture supernatant of E. coli BL21-pET20b-C4ST; 2, SDS-PAGE analysis of culture supernatant of E. coli BL21-pUC19-C4ST; 3, SDS-PAGE analysis of culture supernatant of E. coli BL21-pET20b-C6ST; 4, SDS-PAGE analysis of culture supernatant of E. coli BL21-pUC19-C6ST.

Analysis of C4ST and C6ST activity: The activity of C4ST and C6ST was analysis based on chondroitin. The reaction liquor were 20 mM Tris-HCl (pH7.0), 3 mM PNPS, 20 µM PAP, 10 mg ASST IV, 5 mg/mL chondroitin, and 20 µg C4ST or C6ST. The reaction was happened at 37° C. for 20 h, and terminated by heating at 100° C. for 5 min. At last, the absorbance was determined at 400 nm. The blank was reaction liquor components with no C4ST and C6ST. Product rate was calculation by the formula $Y=10^{-3}*(18.83*(AC-AASST\ IV)+0.38)$; Ac: the absorbance of C4ST or C6ST; ASST IV: the absorbance of blank.

Chondroitin molecular weight analysis: The molecular weight of chondroitin was analysed by combination of Multi-Angle Laser Light Scattering Instrument and Size Exclusion Chromatography with Ultrahydrogel Linea on refractive index detector. It was performed with 0.5 mL/min phase (0.1 M $NaNO_3$) at 50° C. for 20 min and injection volume was 20 µL.

Example 1: The Production of ASST IV, C4ST, and C6ST by Bioengineered E. coli

The genes encoding Rat ASST IV C4ST, and C6ST were separately inserted between the Nde I and Not I sites of pET26b after the T7 promoter and fusing with His-tag in the N-terminal to obtain the engineering plasmids pET26b-C4ST, pET26b-C6ST, and pET26b-ASST IV (The primers used were listed in Tab. 2). Finally, those plasmids were transformed into E. coli BL21 (DE3) and plated on LB plate with 50 µg/mL ampicillin for screening.

The E. coli BL21 separately containing pET26b-C4ST, pET26b-C6ST, and pET26b-ASST IV was cultivated in Luria-Bertani (LB) medium with 50 µg/mL ampicillin at 37° C. in a rotary shake at 220 rpm. Two milliliter of culture was inoculated into 50 mL of LB medium with 50 µg/mL ampicillin and cultivated at 37° C. Then, after 2 h, $OD_{600}$ of the broth reached 0.6-0.8, 30 µL of 0.1 mM IPTG (isopropyl-β-D-thiogalactopyranoside) was add into the broth. After it was induced at 16° C. for 48 h, cells were harvested by centrifugation at 8000 rpm for 5 min at 4° C.

The recombinant E. coli BL21 were washed by 20 mM Tris-HCl (pH7.0), and diluted in 20 mM Tris-HCl (pH7.0) to have an absorbance of 10 at 600 nm. The suspended cells were lysed by sonication at 4° C. The cleared lysate was mixed were separated by 8-12% SDS-PAGE and identified by size comparison to Pre-stained standard (ThermoFisher, Germany) (FIG. 1, 2) and MALDI-TOF-MASS (Shimadzu, Japan).

Example 2: Construction of Bioengineered P. pastoris

Figure 3:
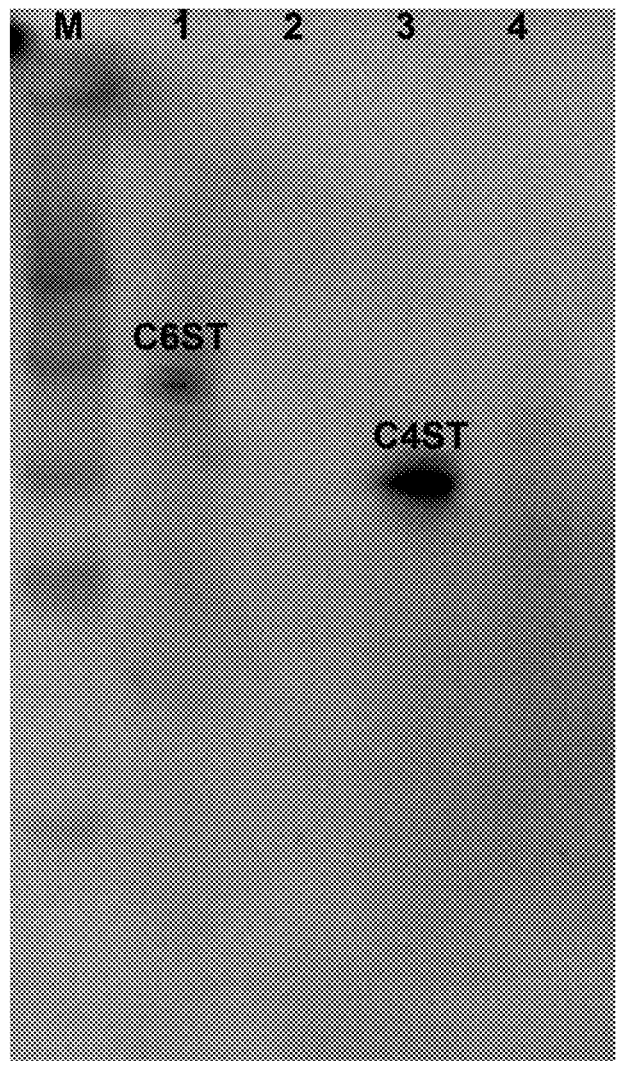
FIG. 3 Western blot analysis of recombinant P. pastoris which expressed C4ST or C6ST; M, marker; 1, Western blot analysis of culture supernatant of recombinant P. pastoris expressing C4ST based on pPIC; 2, Western blot analysis of culture supernatant of recombinant P. pastoris expressing C4ST based on pGAPZ; 3, Western blot analysis of culture supernatant of recombinant P. pastoris expressing C6ST based on pPIC; 4, Western blot analysis of culture supernatant of recombinant P. pastoris expressing C6ST based on pGAPZ.

Genes encoding Rat C4ST, C6ST were amplified by PCR using the PrimeSTAR HS (Premix) with the primes containing the sequence of pPIC3.5K as overlapping overhangs in the 5'-terminal, followed by Gibson isothermal assembly cloning to circularize to obtain the engineering pPIC3.5K-C4ST, and pPIC3.5K-C6ST with alpha signal peptide (The primers used were listed in Table 2). Then, the transformation and recombinant screening were proposed according to the instructions of A Pichia Vector for Multicopy Integration and Secreted Expression (Invitrogen, Germany).

pPIC3.5K-C4ST and pPIC3.5K-C6ST were separately transformed into P. pastoris GS115 to get recombinant P. pastoris GS115. Recombinant P. pastoris GS115 was cultivated in 50 mL BMMY medium containing 0.5 g/L methanol at 20° C., 200 rpm, for 5d. The culture supernatants were collected for C4ST and C6ST purification. The supernatants were filtered through a 0.22 µm membrane and concentrated with Millipore ultrafiltration system according to the manufacturer's instructions with a membrane of 3 kDa cut off, the resulted samples were analysis and identified by SDS and MALDI-FOR-MASS (FIG. 3).

Figure 4:
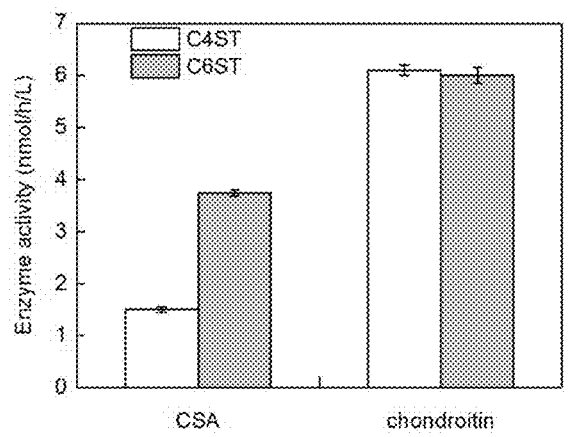
FIG. 4 Activity analysis of C4ST and C6ST based on chondroitin, commercial CSA and CSC from animal.

C4ST and C6ST activity was also assayed by changes of absorbance at 400 nm due to the formation of free 4-nitrophenol as described with some modification (FIG. 4).

Example 3: Synthesis of CSA, CSC

The conversion of chondroitin to CSA or CSC involved two steps, including PAPS regeneration and sulfotransferase modification. In brief, the standard reaction mixture containing 3 mM 3'-phosphoadenosine 5'-phosphate (PNPS), 10 mg ASST IV (0.1-100 nmol/min·mg·protein) and 5 mg/mL chondroitin, and 20 µg C4ST (0.1-100 pmol/min·mg·protein) or C6ST (0.1-100 pmol/min·mg·protein), and 20 mM Tris-HCl (pH7.0) buffer. The mixture was incubated at 37° C. for 20 h for CSA or CSC.

Example 4 CS Disaccharide Fractionation Analysis

Figure 5:
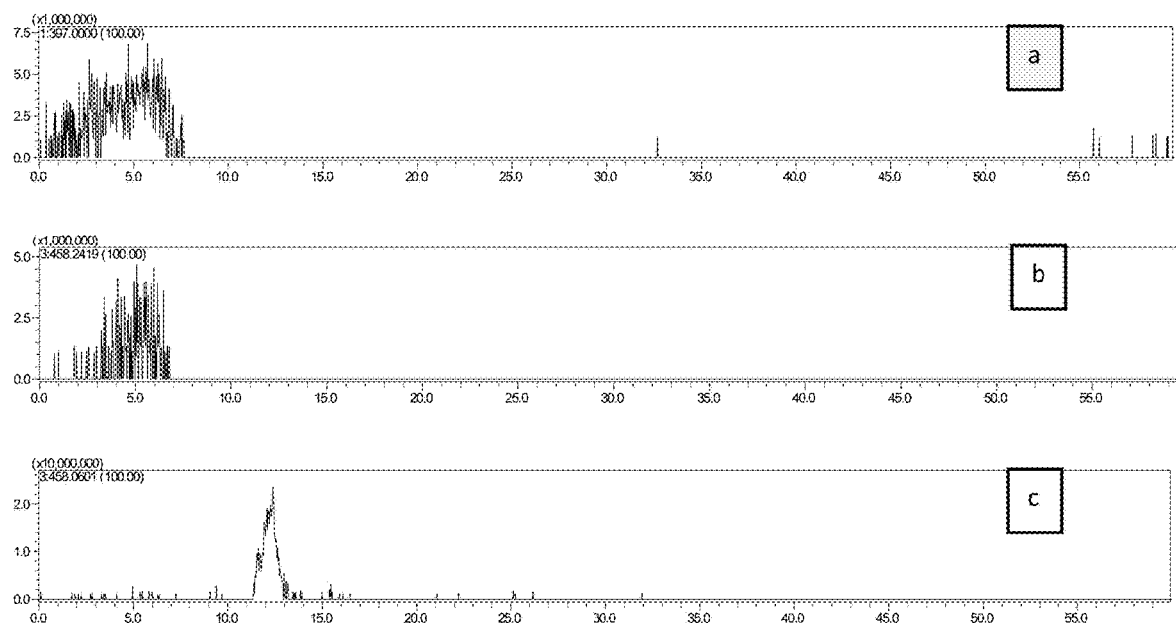
FIG. 5 CS disaccharide fractionation analysis. LC-MS spectra of chondroitin disaccharides (a); LC-MS spectra of CSC disaccharides (b); LC-MS spectra of CSA disaccharides (c).
Figure 6:
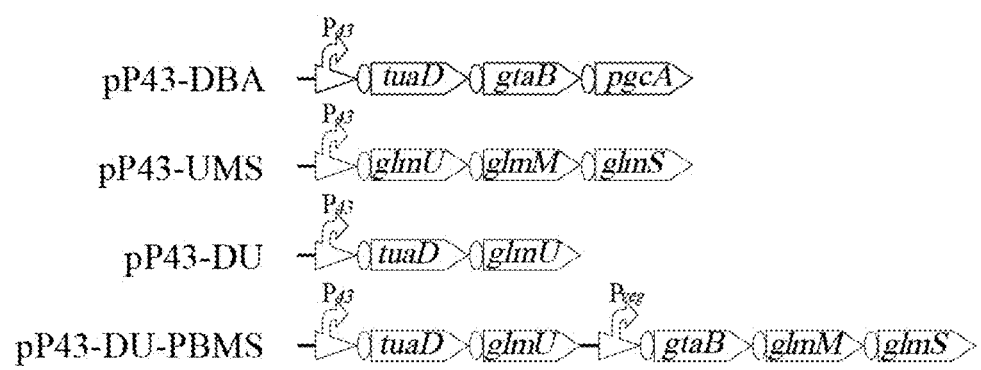
FIG. 6 Schematic of plasmid construction for co-expression of pathway genes in B. subtilis 168.

CS disaccharide fraction was analysed by LCMS after it was lysed by chondroitinase ABC at 37° C. for 5-20 h and terminated at 100° C. for 5 min. The LC were performed at C18 Reverse phase column, 0.3 mm*250 mm, with phase A (8 mM $CH_3COOH$), phase B (8 mM $CH_3COOH$ 70% methanol/$H_2O$). The elution condition was in Table 1. The MS were performed with nitrogen as the desolation gas and as a nebulizer in negative-ion modes. The nebulizer flow was 0.75 L/min and nozzle temperature was 140° C. The $N_2$ was also the drying gas with the flow 1.2 mL/min. The negative ion spectra were generated by scanning the range of 40-2000 m/z, with special ion peaks M/Z 397 and 458 (FIG. 5).

TABLE 1

| Time (min) | PhaseA(%) | PhaseB(%) |
|---|---|---|
| 0 | 100 | 0 |
| 3 | 100 | 0 |
| 13 | 98 | 2 |
| 28 | 86 | 14 |
| 41 | 75 | 25 |
| 57 | 61 | 39 |
| 74 | 45 | 55 |
| 84 | 10 | 90 |
| 104 | 100 | 0 |

| Time (min) | Phase A(%) | Phase B(%) |
|---|---|---|
| 13 | 98 | 2 |
| 28 | 86 | 14 |
| 41 | 75 | 25 |
| 57 | 61 | 39 |
| 74 | 45 | 55 |
| 84 | 10 | 90 |
| 104 | 100 | 0 |

Example 5: Construction of Recombinant *B. subtilis* with Coexpression Pathway Gene At first, *B. subtilis* E168C components were prepared. The inorganic ion components were (g/L): $K_2HPO_4$, 140; $KH_2PO_4$, 60; $(NH_4)_2SO_4$, 20; $(Na_3C_6H_5O_7·2H_2O)$,10; $MgSO_4·7H_2O$, 2. GMI solutions used for component preparation containing 9.7 mL inorganic ions, 2.5 mL 20% glucose, 0.4 mL 5% casein, 1 mL 10% yeast extract per 100 mL. GMII solutions used for component preparation containing 9.7 mL inorganic ions, 2.5 mL 20% glucose, 0.08 mL 5% casein, 0.04 mL 10% yeast extract, 0.25 mL 1M $MgCl_2$, 0.05 mL 1M $CaCl_2$ per 100 mL. In detail, the colony of *B. subtilis* E168C was inoculated in 5 mL GMI, and cultivated at 30° C., 125 rpm for 16 h. Then, it was inoculated into 18 mL GMI with 10% (V/V), and cultivated at 37° C., 200 rpm for 3.5 h. Following, it was inoculated into 90 mL GMII with 10% (V/V), and cultivated at 37° C., 200 rpm for 1.5 h. Then, the cells were collected by centrifugation at 4° C., 5000 g for 10 min, and resuspended in 10 mL GMII, packaged it in 500 µl for each one.

Figure 7:
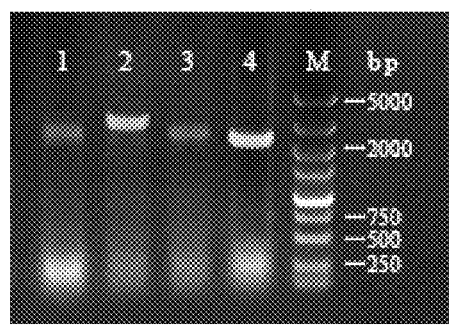
FIG. 7 Electrophoresis analysis of recombinant strains: M, marker; 1, B. subtilis E168C/pP43-DBA; 2, B. subtilis E168C/pP43-UMS; 3, B. subtilis E168C/pP43-DU; 4, B. subtilis E168C/pP43-DU-PBMS.

The recombinant plasmids pP43-DBA, pP43-UMS, pP43-DU, and pP43-DU-PBMS used for co-expression pathway genes were construction based on the parent expression plasmid pP43NMK (Production of specific-molecular-weight hyaluronan by metabolically engineered *Bacillus subtilis* 168, Metabolic Engineering, 2016, Jinpeng). Then, they were transformed into *B. subtilis* E168C components by chemical transformation, and cultured in LB plates with 50 µg/mL kanamycin for transformant selection. All the transformant were confirmed by colony PCR with the primers gtaB-F/pgcA-R, glmM-F/glmS-R, tuaD-F/glmU-R, and glmU-F/gtaB-R. The results of electrophoresis were in FIG. 7. All the recombinant strains were named as *B. subtilis* E168C/pP43-DBA, *B. subtilis* E168C/pP43-UMS, *B. subtilis* E168C/pP43-DU, *B. subtilis* E168C/pP43-DU-PBMS.

```
Primers sequences: 5'-3':

gtaB-F:     ATGAAAAAAGTACGTAAAGCCATAA
            (SEQ ID NO: 7)

pgcA-R:     TTATTTTGCTGTTGACTCAACAA
            (SEQ ID NO: 8)

glmM-F:     ATGGGCAAGTATTTTGGAACAGACG
            (SEQ ID NO: 9)

glmS-R:     TTACTCCACAGTAACACTCTTCGCA
            (SEQ ID NO: 10)

tuaD-F:     GTGAAAAAAATAGCTGTCATTGGAAC
            (SEQ ID NO: 11)

glmU-R:     TTATTTTTATGAATATTTTTCACATAATC
            (SEQ ID NO: 12)

glmU-F:     ATGGATAAGCGGTTTGCAGTTG
            (SEQ ID NO: 13)

gtaB-R:     TTAGATTTCTTCTTTGTTTAGTAAAC
            (SEQ ID NO: 14)
```

Example 6: Production of Chondroitin by Recombinant Strains in Flask

All the four recombinant strains were inoculated into LB with 50 µg/mL kanamycin, cultured at 37° C., 200 rpm for 16 h. Then, they were inoculated with 10% (V/V) into fermentation medium (20 g/L yeast extract, 50 g/L sucrose, 3.9 g/L $K_2SO_4$, 1.5 g/L $MgSO_4$, 50 mM phosphate buffer, pH7.0 50 µg/mL kanamycin), cultured in 37° C., 200 rpm for 54 h. And then, it was induced at the second hours by 20 g/L xylose. All the medium for *B. subtilis* E168C culture have no kanamycin. After fermentation, the culture was centrifugated at 10000 g for 5 min, and the supernatants were collected. Then 3V ethanol were added and mixed at 4° C. for 1 h for the precipitation, after centrifugated at 10000 g for 5 min, the sediment was collected and resuspended in H$_2$O. Then, the centrifugation and resuspend steps were repeats for three times for chondroitin purification. The chondroitin concentration was assayed by Bitter-Muir carbazole assay. 200 μl samples and 1 mL Na$_2$B$_4$O$_2$.10H$_2$O—H$_2$SO$_4$ were mixed in tubes and boiled for 15 min. After they were cooled down, 50 μl carbazole was added and mixed, then boiled for 15 min. The optical density was determined after they were cooled down, and the chondroitin yield was calculated.

Figure 8:
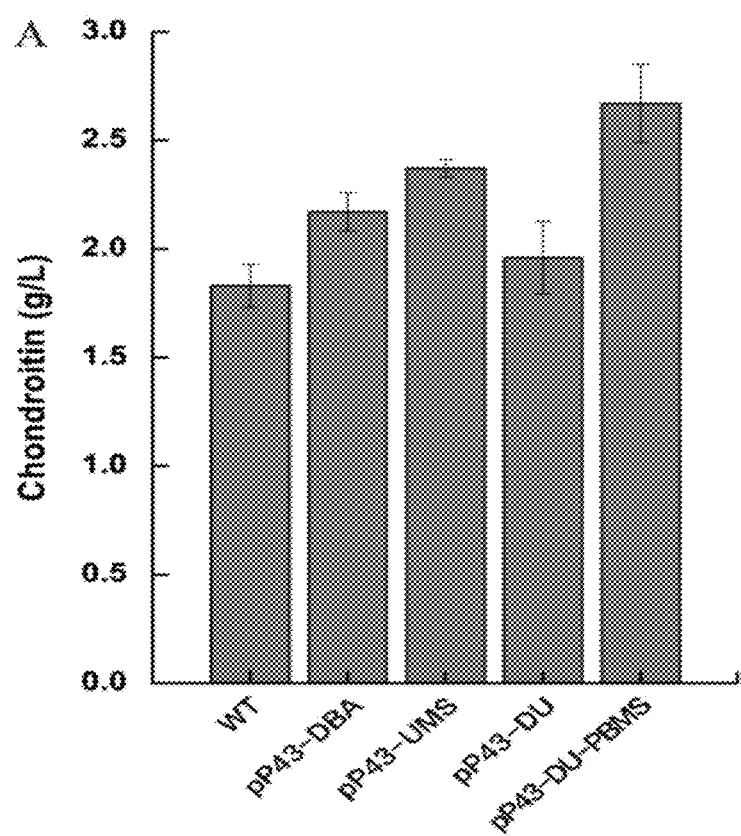
FIG. 8 Production of chondroitin by the recombinant B. subtilis 168.
Figure 9:
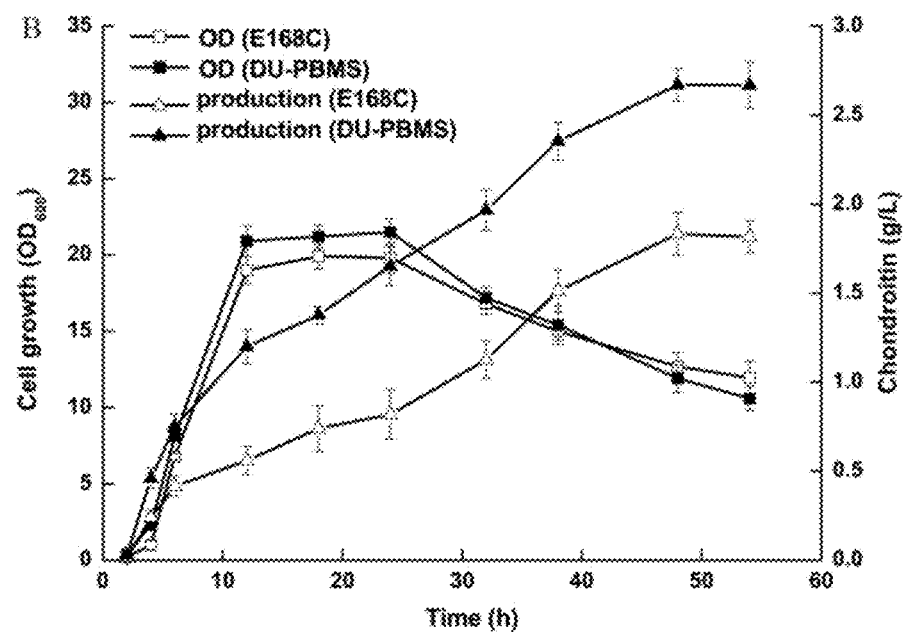
FIG. 9 Time course of chondroitin production and cell growth by B. subtilis E168C/pP43-DU-PBMS and B. subtilis E168C.

The chondroitin yield was increased by recombinant strains (*B. subtilis* E168C/pP43-DBA 2.17 g/L, *B. subtilis* E168C/pP43-UMS 2.37 g/L, *B. subtilis* E168C/pP43-DU 1.96 g/L, *B. subtilis* E168C/pP43-DU-PBMS 2.67 g/L), compared to parent (1.83 g/L) (FIG. 8). It was shown that the recombinant strains which co-expressed all the pathway genes had the highest chondroitin production. It meant that the balance between the concentration of UDP-GlcUA and UDP-GlcNAc contributed to chondroitin synthesis. For strains growth, it was stationary phase for *B. subtilis* E168C/pP43-DU-PBMS culture to the 12-24th hours (FIG. 9). The highest OD$_{600}$ nm of *B. subtilis* E168C/pP43-DU-PBMS culture reached 21.5 while the parents' OD$_{600}$ nm was 19.9. In conclusion, recombinant pP43-DU-PBMS have no effect on strains growth. Besides, the molecular weights of chondroitin produced by recombinant strains (84.36 kDa, 97.02 kDa, 72.78 kDa, and 119.20 kDa) were higher than the parents (83.51 kDa) according to MALLS-SEC (Table 2). The polydispersity Ip of chondroitin was between 1.08-1.51, and the value was closer to 1 when certain UDP-GlcUA and UDP-GlcNAc existed. That means, co-expressing genes related to the synthetic pathway of chondroitin, such as genes related to the synthetic pathway of UDP-glucuronic acid (UDP-GlcUA) or UDP-N-Acetylglucosamine (UDP-GlcNAc) was a successful method for uniformity chondroitin production.

TABLE 2

Difference of chondroitin molecular weight produced by recombinant *B. subtilis*

| Strains | $^{a}M_n$ (kDa) | $^{b}M_w$ (kDa) | $^{c}I_p$ |
|---|---|---|---|
| *B. subtilis* E168C | 69.58 ± 0.62 | 83.51 ± 0.98 | 1.21 ± 0.03 |
| *B. subtilis* E168C/pP43-DBA | 59.83 ± 0.87 | 84.36 ± 1.02 | 1.41 ± 0.04 |

TABLE 2-continued

Difference of chondroitin molecular weight produced by recombinant *B. subtilis*

| Strains | $^{a}M_n$ (kDa) | $^{b}M_w$ (kDa) | $^{c}I_p$ |
|---|---|---|---|
| *B. subtilis* E168C/pP43-UMS | 89.83 ± 0.67 | 97.02 ± 1.88 | 1.08 ± 0.08 |
| *B. subtilis* E168C/pP43-DU | 48.20 ± 1.39 | 72.78 ± 1.60 | 1.51 ± 0.03 |
| *B. subtilis* E168C/pP43-DB-PBMS | 101.02 ± 1.08 | 119.20 ± 2.18 | 1.18 ± 0.02 |

$^{a}$number-average molecular weight($M_n$);
$^{b}$relative molecular mass($M_w$);
$^{c}$polydispersity($I_p = M_w/M_n$).

Example 7: Production of Chondroitin by *B. subtilis* E168C/pP43-DU-PBMS in 3 L Fermenter with Strategy of Feed-Batch

*B. subtilis* E168C/pP43-DU-PBMS was inoculated into 150 mL LB broth, with 50 μg/mL kanamycin and cultivated at 37° C., 200 rpm for 16 h. Then, they were inoculated with 10% (V/V) into fermentation medium (20 g/L yeast extract, 50 g/L sucrose, 3.9 g/L K$_2$SO$_4$, 1.5 g/L MgSO$_4$, 50 mM phosphate buffer, pH7.0 50 μg/mL kanamycin), and cultivated at 37° C., 2 vvm. 2h after the inoculation into fermentation medium, 20 g/L xylose was added. The pH was adjusted to 7.0 by 5 M NaOH. The stirred rate was adjusted to 600 rpm at the 6th hours, and 800 rpm at the 8th hours. 800 g/L sucrose solution was feed when the sucrose concentration of broth bellowed than 5 g/L to keep the sucrose concentration at 0-5 g/L. In detail, the feed strategy was 7.5, 7.5, 15, 10 g/L/h during 8-12 h. After the fermentation, the Mw, Mn, and 1p were assayed by HPSEC-MALLS.

Figure 10:
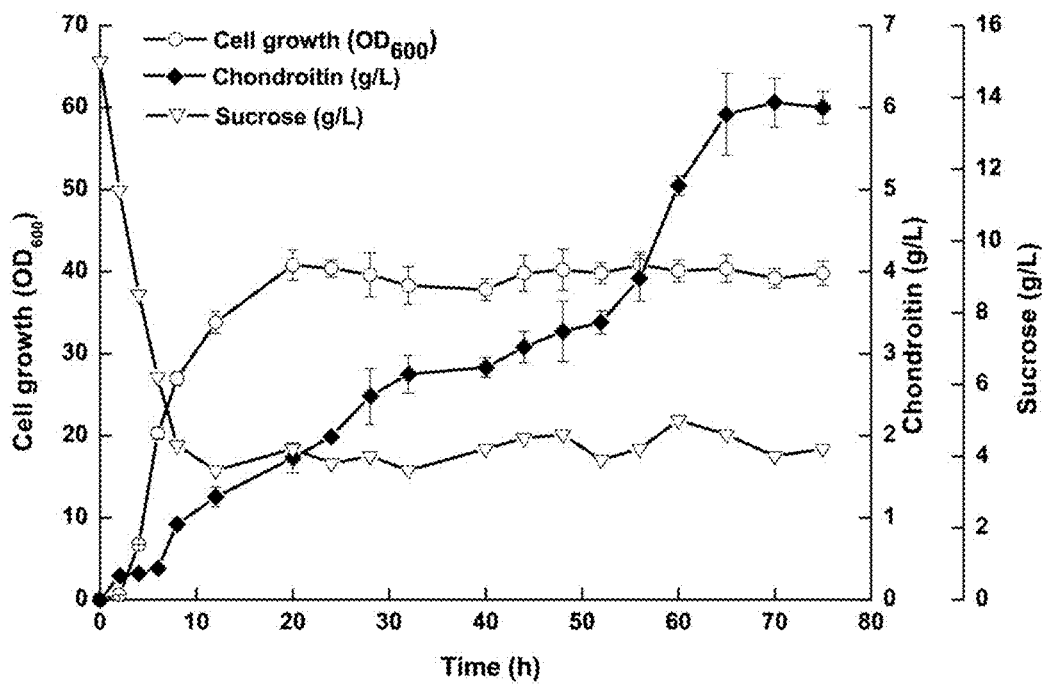
FIG. 10 Time course of chondroitin production with feed-back culture in 3 L fermenter by B. subtilis E168C/pP43-DU-PBMS.

It showed that Time course of chondroitin production was in S style. Chondroitin mainly accumulated during later stationary phase (FIG. 10). And chondroitin accumulation was no couple with strains growth. The highest chondroitin concentration was 6.06 g/L at the 70th which was 2.27 times than chondroitin production in the flask. The Mw of chondroitin in the fermenter was 78.64 kDa which was smaller than that in the flask due to the shearing force caused by stirring. As a result, the 1p of chondroitin produced in fermenter was 1.89 higher than that in the flask. That means the chondroitin molecular weight was more dispersive when fermented in 3 L fermenter.

What is claimed is:

1. A method for biosynthesis of Chondroitin sulfate (CS), comprising:
   expressing in *Escherichia coli* or *Pichia pastoris* a heterogeneous gene encoding chondroitin 4-sulfotransferase (C4ST) and a heterogeneous gene encoding chondroitin 6-sulfotransferase (C6ST); wherein a sequence of the heterogeneous gene encoding C4ST is set forth in SEQ ID NO:15; and wherein a sequence of the heterogeneous gene encoding C6ST is set forth in SEQ ID NO:16;
   collecting the C4ST and C6ST;
   and incubating the C4ST and C6ST with a 3'-phosphoadenosine-5'-phosphosulfate (PAPS) regeneration system for 20-50 hours;
   and wherein the recombinant *Escherichia coli* or the *Pichia pastoris* comprise a recombinant expression plasmid comprising the heterogeneous gene encoding C4ST and the heterogeneous gene encoding C6ST.

2. The method according to claim 1, wherein the plasmid is pET or pPIC.

3. The method according to claim 1,
   wherein the PAPS regeneration system catalyzes p-nitrobenzenesulphonic acid (PNPS) to PAPS, and
   wherein the PAPS regeneration system comprises:
   0.1-100 μg aryl sulfotransferase IV (ASST IV),
   0.1-50 mM PNPS,
   1-200 μM PAP (3'5'-adenosine diphosphate), and
   1-200 mM Tris-HCl, pH 5-9.

4. The method according to claim 3, further comprising expressing ASST IV in *Escherichia coli* encoded on a pET plasmid; wherein a sequence of a gene encoding ASST IV is set forth in SEQ ID NO:17.

5. The method according to claim 1, comprising adding 0.1-100 μg C4ST and C6ST to the PAPS regeneration system for CS synthesis.

6. The method according to claim 3, wherein a specific activity of ASST IV is 0.1-100 nmol/min·mg·protein.

7. The method according to claim 1, wherein a specific activity of C4ST is 0.1-100 pmol/min·mg·protein, and wherein a specific activity of C6ST is 0.1-100 pmol/min·mg·protein.

8. The method according to claim 1, comprising sulfating chondroitin using C4ST and C6ST assisted with the PAPS regeneration system under 25-50° C. within 1-50 hours.

9. The method according to claim 8, comprising producing the chondroitin by a recombinant *Bacillus subtilis* 168 (*B. subtilis* 168); wherein the recombinant *B. subtilis* 168 is constructed by expressing KfoC and KfoA in a genome and co-expressing genes of a synthetic pathway of chondroitin, comprising genes of the synthetic pathway of UDP-glucuronic acid (UDP-GlcUA) or UDP-N-Acetylglucosamine (UDP-GlcNAc).

10. The method according to claim 9, wherein genes of the synthetic pathway of UDP-GlcUA comprise pgcA, gtaB, and tuaD, and wherein genes of the synthetic pathway of UDP-GlcNAc comprise glmS, glmM, and glmU.

11. The method according to claim 9, further comprising co-expressing genes tuaD and glmU, or co-expressing genes tuaD, glmU, gtaB, glmM and glmS.

12. The method according to claim 9, comprising using a plasmid pP43NMK to express genes of the synthetic pathway of chondroitin.

13. The method according to claim 9, comprising culturing the recombinant *B. subtilis* 168 at 37° C. for 24-60 hours to produce the chondroitin, and collecting the chondroitin from a supernatant of the culture; wherein a fermentation medium of the culture comprises 20 g/L yeast extract, 15 g/L or 50 g/L sucrose, 3.9 g/L $K_2SO_4$, 1.5 g/L $MgSO_4$ and 50 mM phosphate buffer, and has a pH of 6.5-7.5.

* * * * *

SEQUENCE LISTING

<160> NUMBER OF SEQ ID NOS: 17

<210> SEQ ID NO 1
<211> LENGTH: 1746
<212> TYPE: DNA
<213> ORGANISM: Bacillus subtilis

<400> SEQUENCE: 1

```
atgacttgga gaaagagcta tgaacgctgg aaacagacag aacatttaga tctggaatta      60
aaagagcgcc ttattgaatt agagggagat gaacaggccc ttgaggactg tttctataaa     120
gaccttgaat tcggtaccgg cggaatgcgc ggggaaatcg gcgccgggac aaatcggatg     180
aatatttaca ctgtgcgcaa agcatcggcc gggtttgcgg catacatctc gaagcaaggt     240
```

```
gaggaagcga aaaaacgggg cgttgtcatt gcttatgatt cccgccataa gtctccggag    300
ttcgcgatgg aagcggcaaa acacttgcg acacaaggca tccaaacata cgtgtttgat    360
gagcttcgcc cgacgccaga gctgtcattc gctgttagac agctgaacgc ttatggtgga    420
attgtggtaa cggcaagcca taacccgcct gaatataacg gctacaaagt atacggggat    480
gatggcggcc agctgcctcc aaaggaagcg gacatcgtca ttgagcaggt aaacgcgatt    540
gaaaatgagc tgacgatcac agtggacgaa gaaaataagt taaagaaaaa aggcttaatc    600
aaaatcatcg gtgaagatat tgataaagtt tatacagaaa aactgacgtc catttctgta    660
catcctgaat tatcggaaga agtagatgta aaggttgttt tcacaccgct gcatggaact    720
gcaaataaac cggtcagacg cggtcttgaa gcactcggct acaaaaatgt aacggttgtc    780
aaagaacagg aactgccgga ttcaaacttc tccactgtta catcgccgaa cccgaaggag    840
catgcggcat tcgaatatgc cattaagctt ggggaggagc agaatgcaga tattctcatc    900
gcgacagatc ctgatgctga ccgcctcggc atcgcggtga aaaacgatca aggcaaatat    960
acagtgctga caggaaacca aaccggagcg ttgctgcttc attacctgct ttctgaaaag    1020
aaaaaacaag gcatcctgcc tgataacggt gttgttctca aaacgatcgt cacaagcgaa    1080
atcggccgtg ctgtagcttc ttcattcggc cttgatacga ttgatacgct gacaggcttt    1140
aagtttatcg gtgaaaagat taaggaatac gaagcatcag gccagtatac cttccaattc    1200
ggttatgaag agagctacgg ttatttaatc ggggattttg cccgcgataa ggacgccatt    1260
caggctgcgc ttttggcagt tgaagtttgc gcgttctata aaaaacaggg aatgtcattg    1320
tatgaggcgc tcatcaatct ctttaacgaa tatggttttt atcgtgaagg gctgaaatcc    1380
ctgacgctga aagcaaaca aggagcagag caaattgaag cgattcttgc ttccttcaga    1440
caaaatccgc cgcagaaaat ggcgggcaaa caggttgtca cagcagaaga ttacgctgta    1500
agcaaacgga cgcttctgac tgaaagcaaa gaagaagcca tcgacttgcc aaaatcaaat    1560
gtattgaaat acttcctgga agacgggtct tggttctgtc tccgtccttc tggaactgag    1620
ccgaaggtta aattttattt cgccgtaaaa gggtcatctt tggaagacag tgaaaagcga    1680
cttgccgtcc tttctgaaga tgtaatgaag acggtggatg aaattgttga gtcaacagca    1740
aaataa                                                             1746
```

<210> SEQ ID NO 2
<211> LENGTH: 879
<212> TYPE: DNA
<213> ORGANISM: Bacillus subtilis

<400> SEQUENCE: 2

```
atgaaaaaag tacgtaaagc cataattcca gcagcaggct taggaacacg ttttcttccg     60
gctacgaaag caatgccgaa agaaatgctt cctatcgttg ataaacctac cattcaatac    120
ataattgaag aagctgttga agccggtatt gaagatatta ttatcgtaac aggaaaaagc    180
aagcgtgcga ttgaggatca ttttgattac tctcctgagc ttgaaagaaa cctagaagaa    240
aaaggaaaaa ctgagctgct tgaaaaagtg aaaaaggctt ctaacctggc tgacattcac    300
tatatccgcc aaaaagaacc taaggtctct ggacatgctg tctggtgcgc acgcaacttt    360
atcggcgatg agccgtttgc ggtactgctt ggtgacgata ttgttcaggc tgaaactcca    420 ggggttgcgcc aattaatgga tgaatatgaa aaaacacttt cttctattat cggtgttcag    480
caggtgcccg aagaagaaac acaccgctac ggcattattg acccgctgac aagtgaaggc    540
```

| | |
|---|---|
| cgccgttatc aggtgaaaaa cttcgttgaa aaaccgccta aaggcacagc accttctaat | 600 |
| cttgccatct taggccgtta cgtattcacg cctgagatct tcatgtattt agaagagcag | 660 |
| caggttggcg ccggcggaga aattcagctc acagacgcca ttcaaaagct gaatgaaatt | 720 |
| caaagagtgt tgcttacga ttttgaaggc aagcgttatg atgttggtga aaagctcggc | 780 |
| tttatcacaa caactcttga atttgcgatg caggataaag agcttcgcga tcagctcgtt | 840 |
| ccatttatgg aaggtttact aaacaaagaa gaaatctaa | 879 |

<210> SEQ ID NO 3
<211> LENGTH: 1386
<212> TYPE: DNA
<213> ORGANISM: Bacillus subtilis

<400> SEQUENCE: 3

| | |
|---|---|
| gtgaaaaaaa tagctgtcat tggaacaggt tatgtaggac tcgtatcagg cacttgcttt | 60 |
| gcggagatcg gcaataaagt tgtttgctgt gatatcgatg aatcaaaaat cagaagcctg | 120 |
| aaaaatgggg taatcccaat ctatgaacca gggcttgcag acttagttga aaaaaatgtg | 180 |
| ctggatcagc gcctgacctt tacgaacgat atcccgtctg ccattcgggc ctcagatatt | 240 |
| atttatattg cagtcggaac gcctatgtcc aaaacaggtg aagctgatt aacgtacgtc | 300 |
| aaagcggcgg cgaaaacaat cggtgagcat cttaacggct acaaagtgat cgtaaataaa | 360 |
| agcacagtcc cggttggaac agggaaactg gtgcaatcta tcgttcaaaa agcctcaaag | 420 |
| gggagatact catttgatgt tgtatctaac cctgaattcc ttcgggaagg gtcagcgatt | 480 |
| catgacacga tgaatatgga gcgtgccgtg attggttcaa caagtcataa agccgctgcc | 540 |
| atcattgagg aacttcatca gccattccat gctcctgtca ttaaaacaaa cctagaaagt | 600 |
| gcagaaatga ttaaatacgc cgcgaatgca tttctggcga caaagatttc ctttatcaac | 660 |
| gatatcgcaa acatttgtga gcgagtcggc gcagacgttt caaaagttgc tgatggtgtt | 720 |
| ggtcttgaca gccgtatcgg cagaaagttc cttaaagctg gtattggatt cggcggttca | 780 |
| tgttttccaa aggatacaac cgcgctgctt caaatcgcaa aatcggcagg ctatccattc | 840 |
| aagctcatcg aagctgtcat gaaacgaac gaaaagcagc gtgttcatat tgtagataaa | 900 |
| cttttgactg ttatgggaag cgtcaaaggg agaaccattt cagtcctggg attagccttc | 960 |
| aaaccgaata cgaacgatgt gagatccgct ccagcgcttg atattatccc aatgctgcag | 1020 |
| cagctgggcg cccatgtaaa agcatacgat ccgattgcta ttcctgaagc ttcagcgatc | 1080 |
| cttggcgaac aggtcgagta ttacacagat gtgtatgctg cgatggaaga cactgatgca | 1140 |
| tgcctgattt taacggattg gccggaagtg aaagaaatgg agcttgtaaa agtgaaaacc | 1200 |
| ctcttaaaac agccagtcat cattgacggc agaaatttat tttcacttga agagatgcag | 1260 |
| gcagccggat acatttatca tctctatcggc cgtcccgctg ttcggggaac ggaaccctct | 1320 |
| gacaagtatt ttccgggctt gccgcttgaa gaattggcta aagacttggg aagcgtcaat | 1380 |
| ttataa | 1386 |

<210> SEQ ID NO 4
<211> LENGTH: 1803
<212> TYPE: DNA
<213> ORGANISM: Bacillus subtilis

<400> SEQUENCE: 4

| | |
|---|---|
| atgtgtggaa tcgtaggtta tatcggtcag cttgatgcga aggaaatttt attaaaaggg | 60 |
| ttagagaagc ttgagtatcg cggttatgac tctgctggta ttgctgttgc caacgaacag | 120 |

```
ggaatccatg tgttcaaaga aaaggacgc attgcagatc ttcgtgaagt tgtggatgcc      180
aatgtagaag cgaaagccgg aattgggcat actcgctggg cgacacacgg cgaaccaagc    240
tatctgaacg ctcacccgca tcaaagcgca ctgggccgct ttacacttgt tcacaacggc    300
gtgatcgaga actatgttca gctgaagcaa gagtatttgc aagatgtaga gctcaaaagt    360
gacaccgata cagaagtagt cgttcaagta atcgagcaat tcgtcaatgg aggacttgag    420
acagaagaag cgttccgcaa aacacttaca ctgttaaaag gctcttatgc aattgcttta    480
ttcgataacg acaacagaga aacgattttt gtagcgaaaa acaaaagccc tctattagta    540
ggtcttggag atacattcaa cgtcgtagca tctgatgcga tggcgatgct tcaagtaacc    600
aacgaatacg tagagctgat ggataaagaa atggttatcg tcactgatga ccaagttgtc    660
atcaaaaacc ttgatggtga cgtgattaca cgtgcgtctt atattgctga gcttgatgcc    720
agtgatatcg aaaaaggcac gtaccctcac tacatgttga agaaacggga tgagcagcct    780
gttgttatgc gcaaaatcat ccaaacgtat caagatgaaa acggcaagct gtctgtgcct    840
ggcgatatcg ctgccgctgt agcggaagcg gaccgcatct atatcattgg ctgcggaaca    900
agctaccatg caggacttgt cggtaaacaa tatattgaaa tgtgggcaaa cgtgccggtt    960
gaagtgcatg tagcgagtga attctcctac aacatgccgc ttctgtctaa gaaaccgctc   1020
ttcattttcc tttctcaaag cggagaaaca gcagacagcc gcgcggtact cgttcaagtc   1080
aaagcgctcg gacacaaagc cctgacaatc acaaacgtac ctggatcaac gctttctcgt   1140
gaagctgact atacattgct gcttcatgca ggccctgaga tcgctgttgc gtcaacgaaa   1200
gcatacactg cacaaatcgc agttctggcg gttcttgctt ctgtggctgc tgacaaaaat   1260
ggcatcaata tcggatttga cctcgtcaaa gaactcggta tcgctgcaaa cgcaatggaa   1320
gctctatgcg accagaaaga cgaaatggaa atgatcgctc gtgaatacct gactgtatcc   1380
agaaatgctt tcttcatcgg acgcggcctt gactacttcg tatgtgtcga aggcgcactg   1440
aagctgaaag agatttctta catccaggca gaaggttttg ccggcggtga gctaaagcac   1500
ggaacgattg ccttgatcga acaaggaaca ccagtattcg cactggcaac tcaagagcat   1560
gtaaacctaa gcatccgcgg aaacgtcaaa gaagttgctg ctcgcggagc aaacacatgc   1620
atcatctcac tgaaaggcct agacgatgcg gatgacagat tcgtattgcc ggaagtaaac   1680
ccagcgcttg ctccgttggt atctgttgtt ccattgcagc tgatcgctta ctatgctgca   1740
ctgcatcgcg gctgtgatgt ggataaacct cgtaaccttg cgaagagtgt tactgtggag   1800
taa                                                                  1803
```

<210> SEQ ID NO 5
<211> LENGTH: 1347
<212> TYPE: DNA
<213> ORGANISM: Bacillus subtilis

<400> SEQUENCE: 5

```
atgggcaagt attttggaac agacggtgta agaggtgtcg ccaatagtga gcttacacct     60
gagctggcct ttaaagtcgg acgtttcggc ggttatgtgc tgacaaaaga caaacaacgt   120
ccaaaagtgc tgataggccg cgatacacgc atctccggcc atatgctgga gggagccctt   180
gtcgccggac ttttatccat tggcgcagaa gtcatgcgcc tgggtgtcat ttctacacca   240
ggtgtatctt atttgacaaa agcgatggat gcagaggcgg cgtcatgat ttccgcttct    300 cataacccag tgcaggataa cggcatcaaa ttctttgggg gagatggatt taagctttct   360
```

```
gatgaacagg aggctgaaat tgagcgcctg atggacgaac ctgaggataa gctgccaaga      420
cctgtcggag cagaccttgg acttgtaaac gattattttg aaggcggaca aaaatatctg      480
caattcttaa aacagacagc tgatgaagat ttcacaggca ttcatgtggc attggactgt      540
gccaatggcg caacgtcatc cttggcgaca cacctgtttg ctgatttaga tgcagatgtt      600
tctacaatgg ggacttcccc gaacggatta aacattaatg acggcgtcgg ttcgactcat      660
cccgaagcgc tcagcgcgtt tgtcaaagag aaaaacgcgg atctcggtct tgcgttcgac      720
ggtgacggcg accgcctgat tgctgtcgat gaaaaaggaa atattgtaga cggcgaccaa      780
atcatgtaca tatgctcaaa acatctgaaa tcagagggcc gtttaaagga tgatacagtg      840
gtttcaaccg tgatgagcaa cctcggcttc tataaggcgc tcgaaaaaga aggcatcaaa      900
agcgtgcaga cagctgtcgg cgaccgctac gtagtagaag caatgaaaaa agacggctac      960
aacgtcggcg gagagcagtc aggacatctt attttccttg attacaacac gacaggggac     1020
ggattattgt ctgctattat gctgatgaac actttaaaag caacaggcaa gccgctgtca     1080
gagcttgcag ctgaaatgca gaagttcccg cagctgttag tcaatgtgag agtgactgat     1140
aaatataaag ttgaagaaaa tgaaaaagta aaagcagtta tttctgaagt tgaaaaagaa     1200
atgaacggcg acgccggat tttggtgcgc ccttcaggaa ctgaaccgct cgtccgtgtc     1260
atggctgaag cgaagacgaa agagctgtgc gatgagtatg tcaatcgcat tgttgaagtc     1320
gtccggtcag aaatgggatt agagtaa                                         1347

<210> SEQ ID NO 6
<211> LENGTH: 1371
<212> TYPE: DNA
<213> ORGANISM: Bacillus subtilis

<400> SEQUENCE: 6
atggataagc ggtttgcagt tgttttagcg gctggacaag gaacgagaat gaaatcgaag       60
ctttataaag tccttcatcc agtttgcggt aagcctatgg tagagcacgt cgtggacgaa      120
gccttaaaat tatctttatc aaagcttgtc acgattgtcg acatggtgc ggaagaagtg       180 aaaaagcagc ttggtgataa aagcgagtac gcgcttcaag caaaacagct tggcactgct      240
catgctgtaa acaggcaca gccatttctt gctgacgaaa aaggcgtcac aattgtcatt      300
tgcggagata cgccgctttt gacagcagag acgatggaac agatgctgaa agaacataca      360
caaagagaag cgaaagctac gattttaact gcggttgcag aagatccaac tggatacggc      420
cgcattattc gcagcgaaaa cggagcggtt caaaaaatag ttgagcataa ggacgcctct      480
gaagaagaac gtcttgtaac tgagatcaac accggtacgt attgttttga caatgaagcg      540
ctatttcggg ctattgatca ggtgtctaat gataatgcac aaggcgagta ttatttgccg      600
gatgtcatag agattcttaa aaatgaaggc gaaactgttg ccgcttacca gactggtaat      660
ttccaagaaa cgctcggagt taatgataga gttgctcttt tcaggcaga acaatttatg      720 aaagagcgca ttaataaacg gcatatgcaa aatggcgtga cgttgattga cccgatgaat      780
acgtatattt ctcctgacgc tgttatcgga agcgatactg tgatttaccc tggaactgtg      840
attaaaggtg aggtgcaaat cggagaagat acgattattg cccctcatac ggagattatg      900
aatagtgcca ttggcagccg tacggttatt aaacaatcgg tagtcaatca cagtaaagtg      960
gggaatgatg taaacatagg accttttgct cacatcagac ctgattctgt catcgggaat     1020
gaagtgaaga tcgggaattt tgtagaaatt aaaaagactc aattcggaga ccgaagcaag     1080
gcatctcatc taagctatgt cggcgatgct gaggtaggca ctgatgtaaa cctgggctgc     1140
```

```
ggttcaatta ctgtcaatta tgatggaaag aataagtatt tgacaaaaat tgaagatggc    1200
gcgtttatcg gctgcaattc caacttggtt gccctgtca cagtcggaga aggcgcttat    1260
gtggcggcag gttcaactgt tacggaagat gtacctggaa aagcacttgc tattgccaga    1320
gcgagacaag taaataaaga cgattatgtg aaaaatattc ataaaaaata a             1371
```

<210> SEQ ID NO 7
<211> LENGTH: 25
<212> TYPE: DNA
<213> ORGANISM: Artificial Sequence
<220> FEATURE:
<223> OTHER INFORMATION: Synthetic DNA

<400> SEQUENCE: 7

```
atgaaaaaag tacgtaaagc cataa                                           25
```

<210> SEQ ID NO 8
<211> LENGTH: 23
<212> TYPE: DNA
<213> ORGANISM: Artificial Sequence
<220> FEATURE:
<223> OTHER INFORMATION: Synthetic DNA

<400> SEQUENCE: 8

```
ttatttgct gttgactcaa caa                                              23
```

<210> SEQ ID NO 9
<211> LENGTH: 25
<212> TYPE: DNA
<213> ORGANISM: Artificial Sequence
<220> FEATURE:
<223> OTHER INFORMATION: Synthetic DNA

<400> SEQUENCE: 9

```
atgggcaagt attttggaac agacg                                           25
```

<210> SEQ ID NO 10
<211> LENGTH: 25
<212> TYPE: DNA
<213> ORGANISM: Artificial Sequence
<220> FEATURE:
<223> OTHER INFORMATION: Synthetic DNA

<400> SEQUENCE: 10

```
ttactccaca gtaacactct tcgca                                           25
```

<210> SEQ ID NO 11
<211> LENGTH: 26
<212> TYPE: DNA
<213> ORGANISM: Artificial Sequence
<220> FEATURE:
<223> OTHER INFORMATION: Synthetic DNA

<400> SEQUENCE: 11

```
gtgaaaaaaa tagctgtcat tggaac                                          26
```

<210> SEQ ID NO 12
<211> LENGTH: 30
<212> TYPE: DNA
<213> ORGANISM: Artificial Sequence
<220> FEATURE:
<223> OTHER INFORMATION: Synthetic DNA

<400> SEQUENCE: 12

```
ttattttta tgaatatttt tcacataatc                                       30

<210> SEQ ID NO 13
<211> LENGTH: 22
<212> TYPE: DNA
<213> ORGANISM: Artificial Sequence
<220> FEATURE:
<223> OTHER INFORMATION: Synthetic DNA

<400> SEQUENCE: 13
atggataagc ggtttgcagt tg                                              22

<210> SEQ ID NO 14
<211> LENGTH: 26
<212> TYPE: DNA
<213> ORGANISM: Artificial Sequence
<220> FEATURE:
<223> OTHER INFORMATION: Synthetic DNA

<400> SEQUENCE: 14
ttagatttct tctttgttta gtaaac                                          26

<210> SEQ ID NO 15
<211> LENGTH: 1059
<212> TYPE: DNA
<213> ORGANISM: artificial sequence
<220> FEATURE:
<223> OTHER INFORMATION: Synthetic DNA

<400> SEQUENCE: 15
atgaagccgg cgctgctgga agtgatgagg atgaacagaa tttgccggat ggtgctggcc     60
acttgcttcg gatcctttat cttggtcatc ttctatttcc aaagtatgtt gcacccagtc    120
atgcggagga accccttcgg tgtggacatc tgctgccgga agggatcgag aagtcccctg    180
caggagctct acaatcccat ccagctggag ctatccaaca ctgccatcct gcaccagatg    240
agacgggacc aggtgacaga cacctgccgg gccaacagtg ccatgagccg caagcgcagg    300
gtgctgaccc ccaacgacct gaagcacctg gtggtggatg aggaccacga actcatctac    360
tgctatgtgc ccaaggtagc gtgcaccaac tggaagaggc tcatgatggt cctgagtggc    420
cggggcaagt acagcgatcc catggagatc ccagccaacg aagcccacgt gtcggccaac    480
ctgaagaccc ttaaccagta cagcatccca gagatcaacc accgcttgaa aagctacatg    540
aagttcctgt tcgtgcggga acccttcgag aggctggtgt ctgcctaccg caacaagttc    600
acgcagaagt acaacacctc cttccacaag cgctacggca ccaagatcat ccgacgccag    660
cggaagaacg ccacgcagga ggccctgcgc aaggggacg atgtcaagtt cgaggagttc    720
gtggcctacc tcatcgaccc ccacacccag cgggaggagc ccttcaacga gcactggcag    780
acggtctact ctctctgcca cccgtgccac atccactacg acctcgtggg caagtatgag    840
acactggagg aggactccaa ttacgtactg cagctggccg gagtgagcgg ctacctgaag    900
ttccccacct atgcaaagtc cacccgaact accgacgaga tgaccacgga gttcttccag    960
aacatcagcg ccgagcacca gacacagctg tacgaagtct acaaactgga ctttttaatg   1020
ttcaactact cagtgccaaa ctacctgaag ttggattag                          1059

<210> SEQ ID NO 16
<211> LENGTH: 1437
<212> TYPE: DNA
<213> ORGANISM: Artificial Sequence
<220> FEATURE:
<223> OTHER INFORMATION: Synthetic DNA
```

<400> SEQUENCE: 16

```
atggcgcccc ctctccccat ggagaaagga ctcgctttgc ctcaggattt ccgggacctt      60
gtacacagcc taaagattcg aggcagatac gtcttgttcc tggcatttgt ggtcatagtt     120
tttatcttca ttgaaaagga aaataaaatc atatccaggg tctccgacaa gctgaagcag     180
atccctcatt tgtggcaga tgccaacagc actgacccag ccctgctctt atcggagaat     240
gcatctctct gtccctgag cgagttggat tccacctttt cccatctgcg gagccgcctg     300
cacaacctga gcctgcagct gggcgtggag ccagcaatgg agagccagga ggctggggca     360
gagaagccat cccagcaggc tggagcaggg acccggcgcc acgtgcttct catggccacc     420
acccgcacgg gttcctcgtt cgtgggcgag ttcttcaacc agcagggcaa tatcttctac     480
ctcttcgagc cactgtggca catcgagcgc accgtgttct ccagcagcg aggcgccagc     540
gcggctggtt cagccttggt ctaccgtgat gtcctcaagc agttgttgct atgcgacctg     600
tatgtgctgg agcccttcat cagccctccg cccgaggacc acttgactca gttcctgttc     660
cgccggggat ccagccgttc actctgcgag gatccggtgt gcacacccct cgtcaagaag     720
gtctttgaga gtaccactg caggaaccgt cgctgcgggc cactcaacgt gaccttggcg     780
ggcgaggcct gccgccgcaa ggaccacgtg ccctcaagg ctgtgcgcat ccgtcagctg     840
gagttcctgc agccgctagt tgaggaccg aggttggatc tacgagtcat tcagctggtg     900
cgcgacccc gggccgtgct ggcttcacgc atagtggcct ttgcgggcaa gtatgagaac     960
tggaagaagt ggctgtccga ggggcaggac cagctgagcg aggatgaggt gcagcgattg    1020
cggggcaact gtgagagcat ccgcctgtct gcagagctgg gcttgcggca ccagcctgg    1080
ctgcgcggtc gttacatgct ggtgcgctat gaggatgtgg cacgcaggcc actgcagaag    1140
gcccgagaga tgtacagctt tgcgggcatc cccttgaccc cgcaggtgga ggactggatc    1200
cagaagaaca cgcaggcgac acgcgacagc agcgatgtct actccactca gaaaaactct    1260
tctgagcagt ttgagaagtg cgcttcagc atgcctttca agctggcaca ggtggtacag    1320
gctgcctgtg cccgaccat gcacctcttt ggctacaagt tggccaggga tgccgcctca    1380
ctcaccaacc gctccatcag cctgctggag gagcggggca ccttctgggt cacgtag       1437
```

<210> SEQ ID NO 17  
<211> LENGTH: 876  
<212> TYPE: DNA  
<213> ORGANISM: Artificial Sequence  
<220> FEATURE:  
<223> OTHER INFORMATION: Synthetic DNA

<400> SEQUENCE: 17

```
atggagttct cccgtccacc gctagtgcat gtgaagggta tcccactcat caaatacttt      60
gcagagacaa ttgggccatt gcagaacttc acagcctggc ctgatgactt gctgatcagc     120
acataccaa gtctggtac tacctggatg agtgagatcc tggatatgat ctatcagggt     180
ggcaagctag agaagtgtgg ccgcgccccc atctatgccc gggtacccct ccttgagttc     240
aaatgtccag gggttccctc aggtcttgaa actttggaag agacaccagc cccacggctc     300
cttaagacac atctgcccct gtccttgctc cctcagagtc tgctggatca gaaggtcaag     360
gtgatctaca ttgcccgaaa tgcaaaggat gtggttgtct cctattataa cttctacaac     420
atggccaagc tgcaccctga tccaggcacc tgggacagct tcttgagaa cttcatggat     480
ggggaagtgt cctatgggtc gtggtaccag cacgtgaagg agtggtggga gctgagacac    540
```

```
actcaccctg ttctctatct cttctatgaa gacataaagg agaacccccaa aagggagatc      600 aagaagattc tagagttttt ggggcgctct ctacccgagg agactgtgga ttccattgtt      660
caccacacat ctttcaagaa aatgaaagag aactgcatga ctaactacac aaccatcccc      720
actgagatta tggaccacaa tgtttctccc ttcatgagga aaggtactac tggggactgg      780
aaaaatacct tcactgtagc ccagaatgag cgctttgatg cccactatgc taagacaatg      840
acagattgtg acttcaagtt tcgttgtgaa ctatga                                876
```